(12) United States Patent
Chen

(10) Patent No.: US 6,938,833 B2
(45) Date of Patent: Sep. 6, 2005

(54) VEHICLE AIR FRESHENER

(76) Inventor: Hsiang Mei Chen, 25-1, Hua Xi Rd., Da Liao Shiang, Kaohsiung Hsien (TW)

( * ) Notice: Subject to any disclaimer, the term of this patent is extended or adjusted under 35 U.S.C. 154(b) by 119 days.

(21) Appl. No.: 10/717,340

(22) Filed: Nov. 18, 2003

(65) Prior Publication Data

US 2005/0104236 A1 May 19, 2005

(51) Int. Cl.⁷ ................................................ A61L 9/00
(52) U.S. Cl. ........................... 239/44; 40/310; 446/267; 446/325; 446/396; 261/DIG. 88
(58) Field of Search .................... 239/44, 55; 40/310, 40/409; 446/267, 325, 396; 261/107, DIG. 88

(56) References Cited

U.S. PATENT DOCUMENTS

| | | | | |
|---|---|---|---|---|
| 1,647,175 A | * | 11/1927 | Grunberg | 215/370 |
| 4,739,928 A | * | 4/1988 | O'Neil | 239/45 |
| 6,165,041 A | * | 12/2000 | Lin | 446/267 |
| 6,179,219 B1 | * | 1/2001 | Lin | 239/44 |
| 2003/0098362 A1 | * | 5/2003 | Chuang | 239/44 |

* cited by examiner

Primary Examiner—Robert A. Hopkins
(74) Attorney, Agent, or Firm—Pro-Techtor Int'l Services

(57) ABSTRACT

A vehicle air freshener is constructed to include a bottle holding a color fluid and a volatile liquid perfume floating on the color fluid, a socket fastened to the bottle neck of the bottle to hold an absorptive core member that dissipates the volatile liquid perfume into air outside the bottle, a weight-attached ornament set in the volatile liquid perfume and the color fluid, a base fastened to the bottom side of the bottle and adapted to support the vehicle air freshener on a surface; and a bottle cap fastened to the bottle neck of the bottle around the socket, the bottle cap having a center through hole, which receives the bottleneck of the bottle, and a plurality of wire holes for mounting cord members.

3 Claims, 5 Drawing Sheets

VEHICLE AIR FRESHENER

BACKGROUND OF THE INVENTION

1. Field of the Invention

The present invention relates to a vehicle air freshener and, more particularly, to such a vehicle air freshener that functions as a toy tumbler when dissipating a volatile liquid perfume into the air inside the vehicle.

2. Description of the Related Art

Various vehicle air fresheners have been disclosed, and have appeared on the market. These vehicle air fresheners may be fastened to a flat surface inside a vehicle or hung on the output port of the air conditioner of a vehicle. They commonly hold a volatile liquid perfume that gives a good smell after removal of the sealing cap from the container body. These conventional air fresheners are simply designed to dissipate a volatile liquid perfume into air. Due to static design, these conventional air fresheners do not attract much the consumers' attention.

SUMMARY OF THE INVENTION

The present invention has been accomplished under the circumstances in view. It is one object of the present invention to provide vehicle air freshener, which oscillates like a toy tumbler and dissipates a volatile liquid perfume into the air inside the vehicle during running of the vehicle.

To achieve this and other objects of the present invention, the vehicle air freshener comprises a bottle, the bottle having a downwardly protruded bottom mounting flange and a socket sealed to a bottle neck thereof; a fluid filled in the bottle; a volatile liquid perfume filled in the bottle and floating on the fluid, the volatile liquid perfume having a gravity smaller than the fluid; an absorptive core member mounted in the socket and extended to the volatile liquid perfume and adapted to dissipate the volatile liquid perfume into air outside the bottle; an ornament mounted inside the bottle and dipped in the volatile liquid perfume and the fluid, the ornament having a bottom side fixedly mounted with a weight; a base fastened to the downwardly protruded bottom mounting flange of the bottle and disposed in flush with the periphery of said bottle; and a bottle cap fastened to the bottle neck of the bottle around the socket, the bottle cap having a center through hole adapted to accommodate the bottleneck of the bottle, and a plurality of wire holes for mounting cord members.

DETAILED DESCRIPTION OF THE PREFERRED EMBODIMENT

Figure 1:
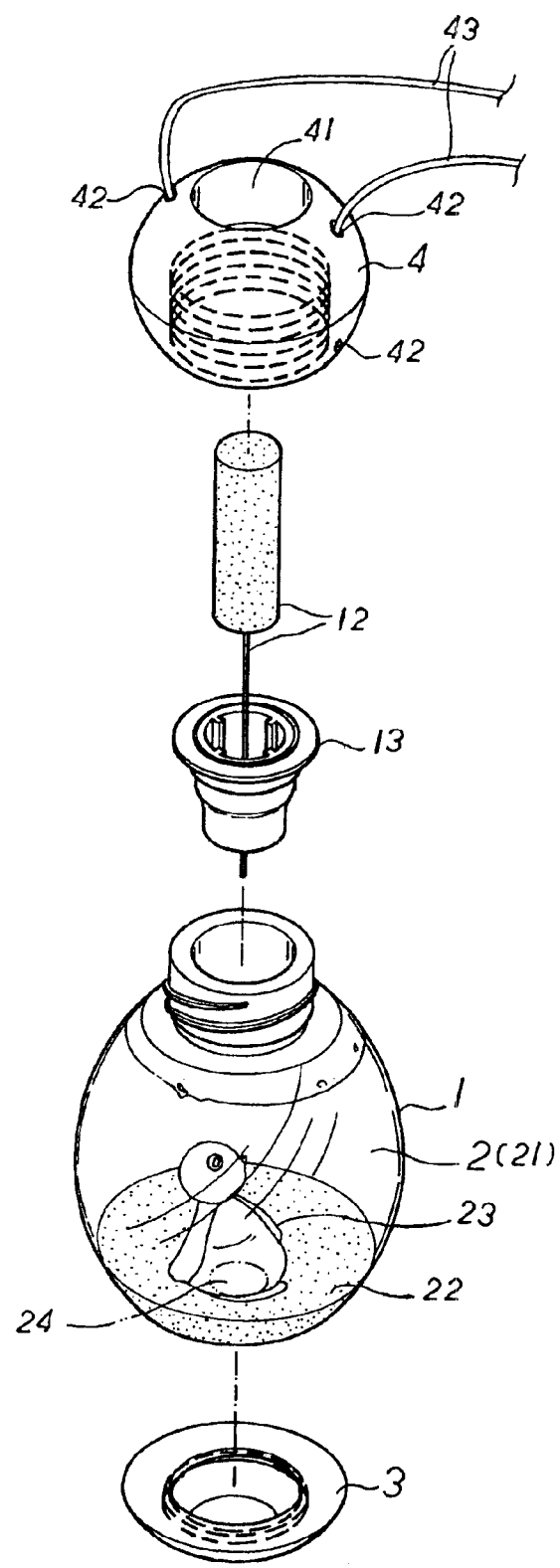
FIG. 1 is an exploded view of a vehicle air freshener according to the present invention.

Referring to FIG. 1, a vehicle air freshener in accordance with the present invention is shown comprised of a bottle 1, filling materials 2, a base 3, and a bottle cap 4.

Figure 3:
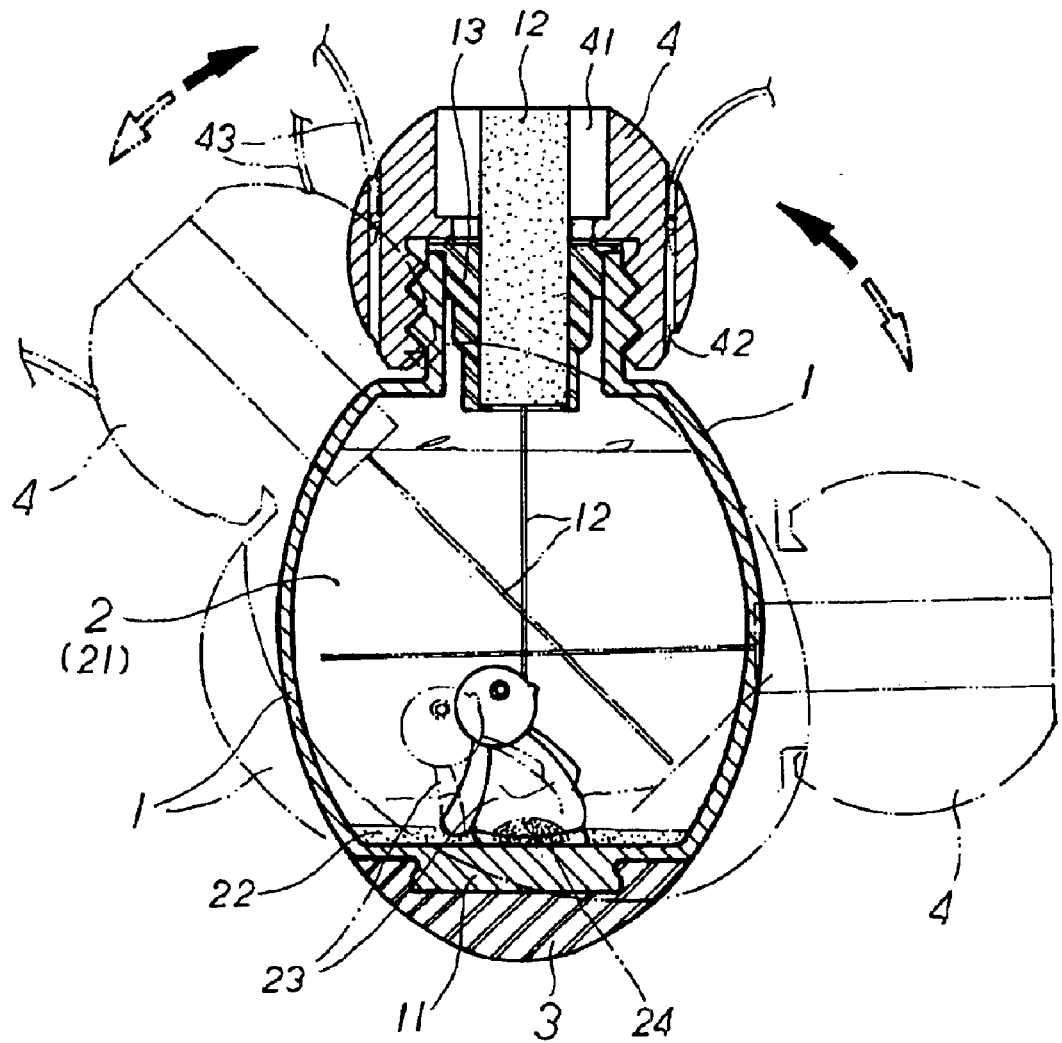
FIG. 3 is a schematic sectional view showing the vehicle air freshener oscillated on a flat surface according to the present invention.
Figure 5:
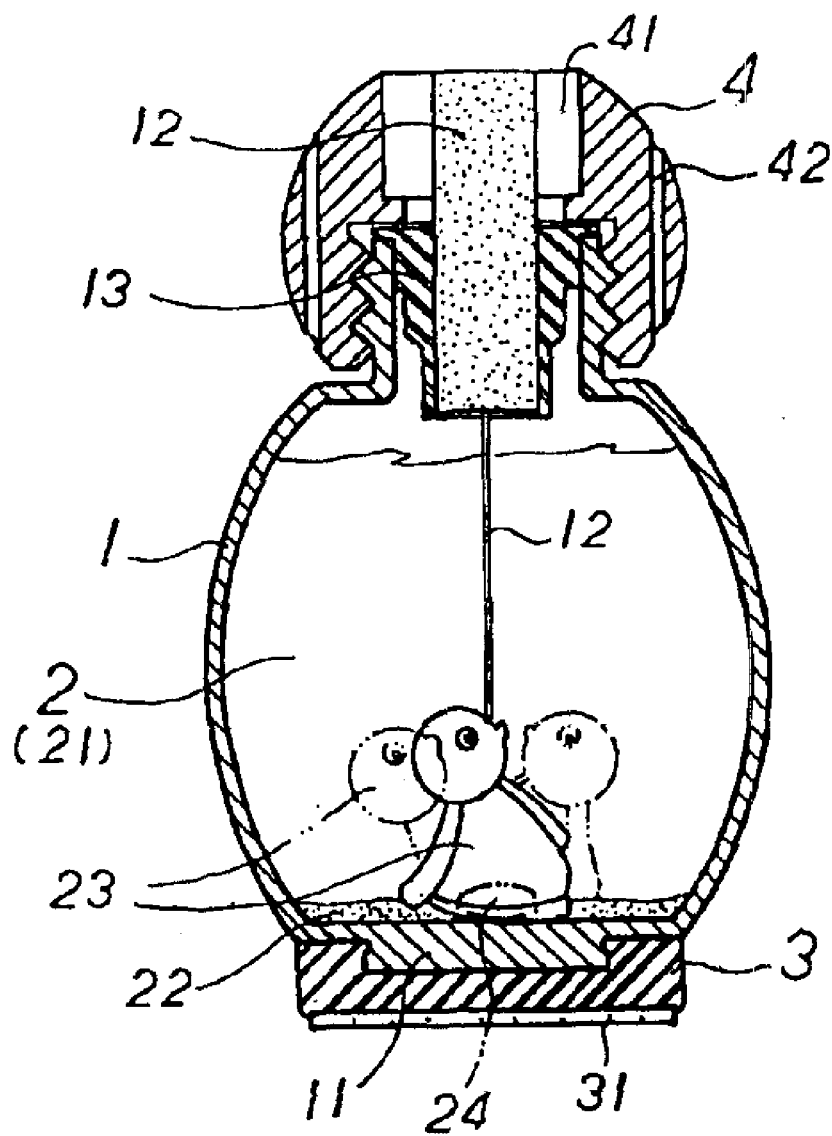
FIG. 5 is a schematic sectional view of the vehicle air freshener shown in FIG. 4.

Referring also to FIGS. 3 and 5, the bottle 1 has a downwardly protruded bottom mounting flange 11 press-fitted into the recessed top side of the base 3, a socket 13 sealed to the bottle neck to hold an absorptive core member 12, which has a bottom end extended to the inside space of the bottle 1.

The filling materials 2 are put in the bottle 1, including a first fluid 21, a second fluid 22, and an ornament 23. The first fluid 21 is a perfume of gravity relatively smaller than the second fluid 21. The second fluid 22 can be water. If desired, the second fluid can be colored with a color substance. The ornament 23 has a weight 24 at the bottom side. The weight 24 holds the ornament 23 in the second fluid 22 and the first fluid 21, enabling the ornament 23 to be oscillated with the second fluid 22 and the first fluid 21 inside the bottle 1. The ornament 23 can be made having the shape of any of a variety of animals. The weight 24 is shaped, for example, like a fish.

Figure 2:
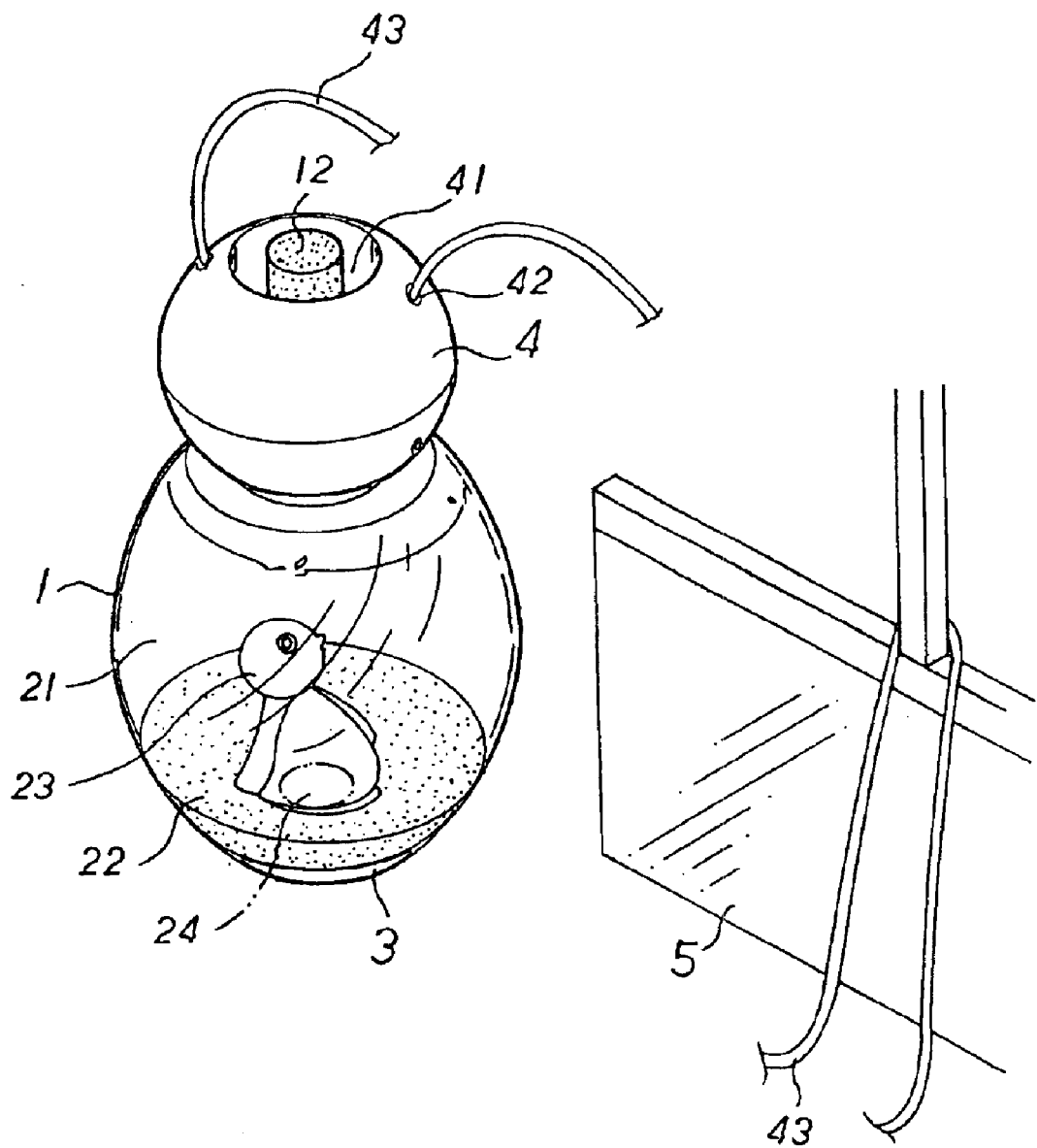
FIG. 2 is a perspective assembly view of the vehicle air freshener according to the present invention.
Figure 4:
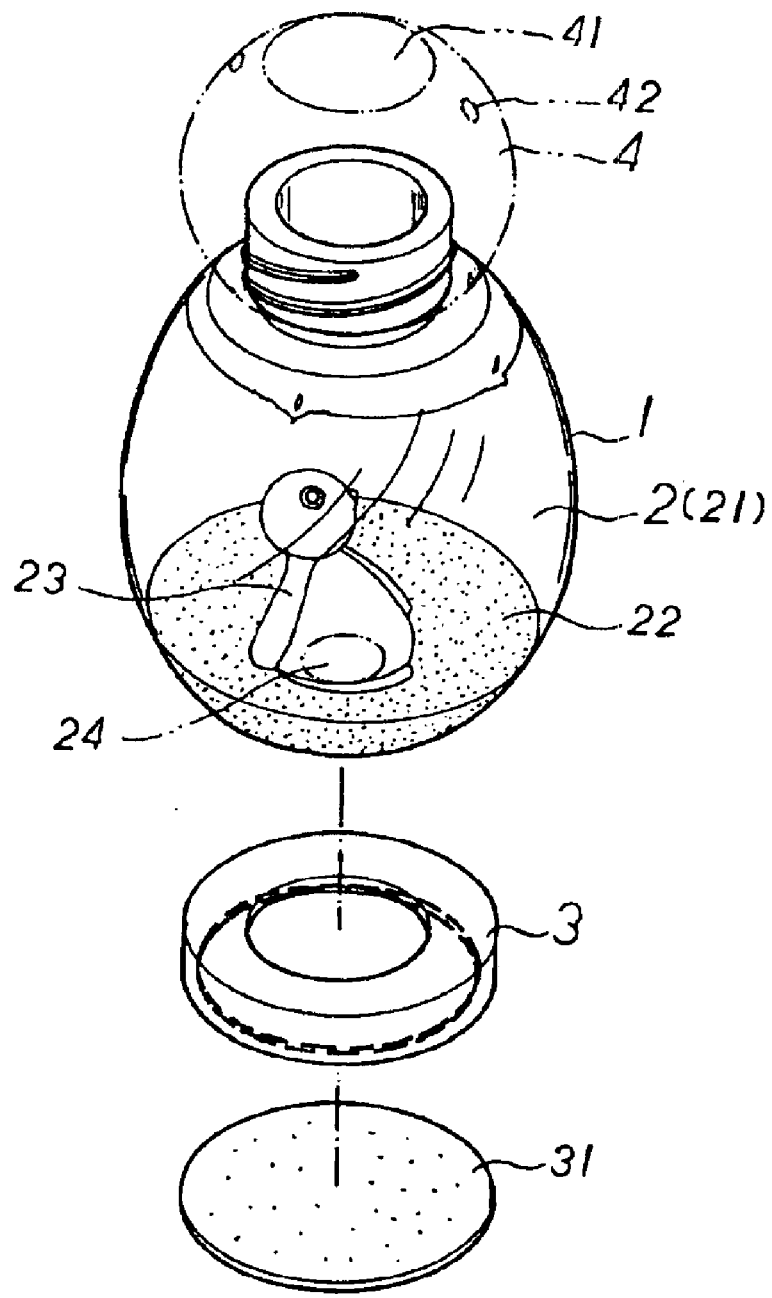
FIG. 4 is an exploded view of an alternate form of the vehicle air freshener according to the present invention.

The base 3 is preferably injection-molded from plastics. When fastened to the downwardly protruded bottom mounting flange 11, the base 3 is maintained in flush with the periphery of the bottle 1. The base 3 can be made having a smoothly curved bottom surface such that the vehicle air freshener functions as a toy tumbler (see FIGS. 2 and 3). Alternatively, the base 3 can be made having a flat bottom surface (see FIGS. 4 and 5) mounted with a double-sided adhesive tape 31 for fastening to a flat surface inside a vehicle.

The bottle cap 4 has a center through hole 41 that is fastened to the bottleneck of the bottle 1 around the socket 11, and a plurality of wire holes 42. Cord members 49 may be fastened to the wire holes 42 for securing the vehicle air freshener to the internal rear-view mirror 5 inside a vehicle.

As indicated above, the user can use a double-sided adhesive tape 31 to fasten the vehicle air freshener to a flat surface inside the vehicle, or use cord members 49 to secure the vehicle air freshener to the internal rear-view mirror of the vehicle. When the user is driving the vehicle, the good smell is dissipated into the air inside the vehicle through the core member 12. In the embodiment shown in FIG. 3, the vehicle air freshener functions as a toy tumbler, the vehicle air freshener oscillates without falling during running of the vehicle.

A prototype of vehicle air freshener has been constructed with the features of FIGS. 1~5. The vehicle air freshener functions smoothly to provide all of the features discussed earlier.

Although particular embodiments of the invention have been described in detail for purposes of illustration, various modifications and enhancements may be made without departing from the spirit and scope of the invention.

What the invention claimed is:

1. A vehicle air freshener comprising:

a bottle, said bottle having a downwardly protruded bottom mounting flange and a socket sealed to a bottleneck thereof;

a fluid filled in said bottle;

a volatile liquid perfume filled in said bottle and floating on said fluid, said volatile liquid perfume having a gravity smaller than said fluid;

an absorptive core member mounted in said socket and extended to said volatile liquid perfume and adapted to dissipate said volatile liquid perfume into air outside said bottle;

an ornament mounted inside said bottle and dipped in said volatile liquid perfume and said fluid, said ornament having a weight fixedly secured to a bottom side thereof;

a base fastened to the downwardly protruded bottom mounting flange of said bottle; and a bottle cap fastened to the bottle neck of said bottle around said socket, said bottle cap having a center through hole adapted to accommodate the bottleneck of said bottle, and a plurality of wire holes for mounting cord members.

2. The vehicle air freshener as claimed in claim 1, wherein said base has a flat bottom surface mounted with a double-sided adhesive tape for fastening.

3. The vehicle air freshener as claimed in claim 1, wherein said second fluid is colored with a color substance.

* * * * *